US00PP11024P

United States Patent [19]

Enthoven

[11] Patent Number: Plant 11,024

[45] Date of Patent: Aug. 3, 1999

[54] GERANIUM PLANT NAMED 'MERISNOW'

[75] Inventor: Adrianus W. M. Enthoven, Wateringen, Netherlands

[73] Assignee: Enthoven Breeding B.V., Wateringen, Netherlands

[21] Appl. No.: 09/044,757

[22] Filed: Mar. 20, 1998

[51] Int. Cl.[6] ..... A01H 5/00

[52] U.S. Cl. ..... Plt./326

[58] Field of Search ..... Plt./325, 326

[56] References Cited

U.S. PATENT DOCUMENTS

P.P. 10,012 11/1997 Lemon ..... Plt./326
P.P. 10,398 5/1998 Trees ..... Plt./326

*Primary Examiner*—Howard J. Locker
*Attorney, Agent, or Firm*—C. A. Whealy

[57] ABSTRACT

A new and distinct variety of Geranium plant named 'Merisnow', characterized by its rounded and compact growth habit; moderate growth rate and vigor; fast rooting; dark green foliage color with distinct zonation pattern; numerous peduncles with ten to twelve flowers per umbel; semi-double pure white flowers; and good weather tolerance.

2 Drawing Sheets

BACKGROUND OF THE INVENTION

The present invention relates to a new and distinct variety of Geranium plant, botanically known as *Pelargonium× hortorum,* and hereinafter referred to by the name 'Merisnow'.

The new Geranium is a product of a planned breeding program conducted by the inventor in Wateringen, The Netherlands. The objective of the breeding program was to develop compact Geranium varieties with semi-double flowers, fast rooting, good flower form, tolerance to Botrytis, weather resistance, compact and pendant growth habit, and attractive flower and foliage colors.

The new Geranium originated from a cross made by the inventor of two proprietary seedling selections identified as code number A111 as the female, or seed, parent and code number A234 as the male, or pollen, parent. The new Geranium was discovered and selected by the inventor as a flowering plant within the progeny of the stated cross in a controlled environment in Wateringen, The Netherlands, in June, 1995.

Compared to plants of the male parent, plants of the new Geranium are taller. Additionally, plants of the new Geranium have a distinct zonation pattern on the foliage whereas plants of the male parent are devoid of a zonation pattern.

Compared to plants of the female parent, plants of the new Geranium are more compact and have a less distinct zonation pattern on the leaves. Additionally, plants of the new Geranium have semi-double flowers whereas plants of the female parent have single flowers.

Asexual reproduction of the new Geranium by terminal cuttings taken at Wateringen, The Netherlands, has shown that the unique features of this new Geranium are stable and reproduced true to type in successive generations of asexual reproduction.

SUMMARY OF THE INVENTION

The following traits have been repeatedly observed and are determined to be the unique characteristics of 'Merisnow'. These characteristics in combination distinguish 'Merisnow' as a new and distinct Geranium:

1. Rounded and compact growth habit.
2. Moderate growth rate and vigor.

3. Fast rooting.
4. Dark green foliage color with distinct zonation pattern.
5. Numerous peduncles with ten to twelve flowers per umbel.
6. Semi-double pure white flowers.
7. Good weather tolerance.

The new Geranium can be compared to the Geranium variety 'Fisalb' (disclosed in U.S. Plant Pat. No. 9,761). Compared to plants of 'Fisalb', plants of the new Geranium flower earlier, have shorter and more numerous peduncles, and have a less intense zonation pattern on the foliage.

BRIEF DESCRIPTION OF THE PHOTOGRAPHS

The accompanying colored photographs illustrate the overall appearance of the new Geranium, showing the colors as true as it is reasonably possible to obtain in colored reproductions of this type.

The photograph on the first sheet comprises a side perspective view of a typical plant of 'Merisnow'.

The photograph at the top of the second sheet comprises a close-up view of a typical flower of 'Merisnow'.

The photographs at the bottom of the second sheet comprises a close-up view of typical leaves, upper surface is on the left and lower surface is on the right. Foliage and flower colors in the photograph may appear different from the actual colors due to light reflectance.

DETAILED BOTANICAL DESCRIPTION

The new Geranium has not been observed under all possible environmental conditions. The phenotype may vary somewhat with variations in environment such as temperature and light intensity, without, however, any variance in genotype. The following observations, measurements and comparisons describe plants grown in Wateringen, The Netherlands, under commercial practice in a glass-covered greenhouse with day temperatures of 20° C. and night temperatures of 18° C. and light levels of 450 W/m2.

In the following description, color references are made to The Royal Horticultural Society Colour Chart except where general terms of ordinary dictionary significance are used.

Classification:

*Botanical.*—*Pelargonium×hortorum* 'Merisnow'.

*Commercial.*—Zonal Geranium.

Parentage:

*Male parent.*—Proprietary seedling selection code number A234.

*Female parent.*—Proprietary seedling selection code number A111.

Propagation:

*Type cutting.*—Terminal cuttings.

*Time to initiate and develop roots.*—Summer: About 16 days at 20° C. Winter: About 16 to 20 days at 20° C.

*Rooting habit.*—Vigorous, fast to root, freely branching.

Plant description:

*General appearance.*—Rounded and compact growth habit. Appropriate for 10.5 to 12 cm containers. About 12 weeks are required to produce a finished plant from an unrooted cutting.

*Growth rate.*—Moderate.

*Vigor.*—Moderate.

*Plant height.*—About 16 cm from soil surface to leaf plane; about 20 cm from soil surface to top of umbels.

*Branching habit.*—Moderate. Pinching (removal of terminal apices) is usually not required.

*Internode length.*—About 2.5 cm.

*Lateral branch lengh.*—About 18 cm.

*Foliage description.*—Arrangement: Alternate. Shape: Reniform. Length: About 4.1 cm. Width: About 7.5 cm. Texture: Velvety, slightly pubescent on both surfaces. Margin: Bicrenate. Zonation: Distinct, about 1.75 cm in width and about 7.5 mm from margin and about 2 cm from petiole. Aspect: Flat, but undulating towards the margin. Color: Upper surface: 139A. Lower surface: 137B. Zonation, upper surface only: Darker than 139A. Venation pattern: Palmate. Petiole: Length: About 6 cm. Diameter: About 4 mm. Color: 146A/146B. Durability to rain, wind and stress conditions: Very good.

Flowering description:

*Flowering habit.*—Flowers arranged in umbels.

*Natural flowering season.*—Spring throughout summer.

*Flower longevity.*—Flowers last about 2.5 weeks on the plant. Flowers self-cleaning.

*Flowers borne.*—Flower buds develop in apical leaf axils. Umbels are displayed above the foliage.

*Umbels.*—Form: Rounded. Quantity of flowers: Usually about 11 per umbel. Diameter: About 9 cm. Depth (height): About 4.75 cm.

*Flowers.*—Form: Semi-double. Diameter: About 3.5 cm. Depth (height): About 2 cm. Quantity of petals and petaloids per flower: About 8.

*Petals.*—Shape: Upper petals: Obtuse. Lower petals: Obovate. Apex: Rounded or slightly incised. Arrangement: Rosette, overlapping. Aspect: Mostly flat. Length: About 2.7 cm. Width: About 1.7 cm. Texture: Satiny, smooth. Margin: Entire. Color: Opened flower, upper petals, upper surface: 155D. Opened flower, upper petals, lower surface: 155D. Opened flower, lower petals, upper surface: 155D. Opened flower, lower petals, lower surface: 155D.

*Petaloids.*—Shape: Irregular, generally obovate with rounded or slightly incised apex. Quantity: Usually 2 to 5 per flower. Arrangement: Rosette, overlapping. Length: About 1.75 cm. Width: About 1.5 cm. Texture: Satiny, smooth. Margin: Entire. Color: Upper surface: 155D. Lower surface: 155D.

*Peduncle* (*umbel stem*).—Angle: Erect. Length: About 11 cm. Diameter: About 5 mm. Texture: Pubescent. Color: Medium green with reddish overtones.

*Pedicel* (*individual flower stem*).—Angle: Between 45 to 90° from vertical. Length: About 2.3 cm. Diameter: About 2 mm. Texture: Pubescent. Color: Medium to light green.

*Flower bud.*—Shape: Elongated ovoid. Length: About 1 cm. Diameter: About 6 mm. Color: Medium to light green.

*Sepals.*—Shape: Narrowly lanceolate with acuminate apex and entire margin. Quantity: 5. Length: About 1.1 cm. Width: About 2 mm. Color: Light green with slight reddish tones.

*Reproductive organs.*—Androecium: Anther shape: Oblong. Anther size: About 1.5 mm. Anther color: 42C/42D. Pollen color: 42C/42D. Gynoecium: Pistil length: About 8 mm. Stigma shape: Decurrent. Stigma color: 193B. Style length: About 4 mm. Style color: 193B.

Disease resistance: No fungal, bacterial nor viral problems observed under commercial conditions.

Seed development: Seed production is very rarely observed.

It is claimed:

1. A new and distinct variety of Geranium plant named 'Merisnow', as illustrated and described.

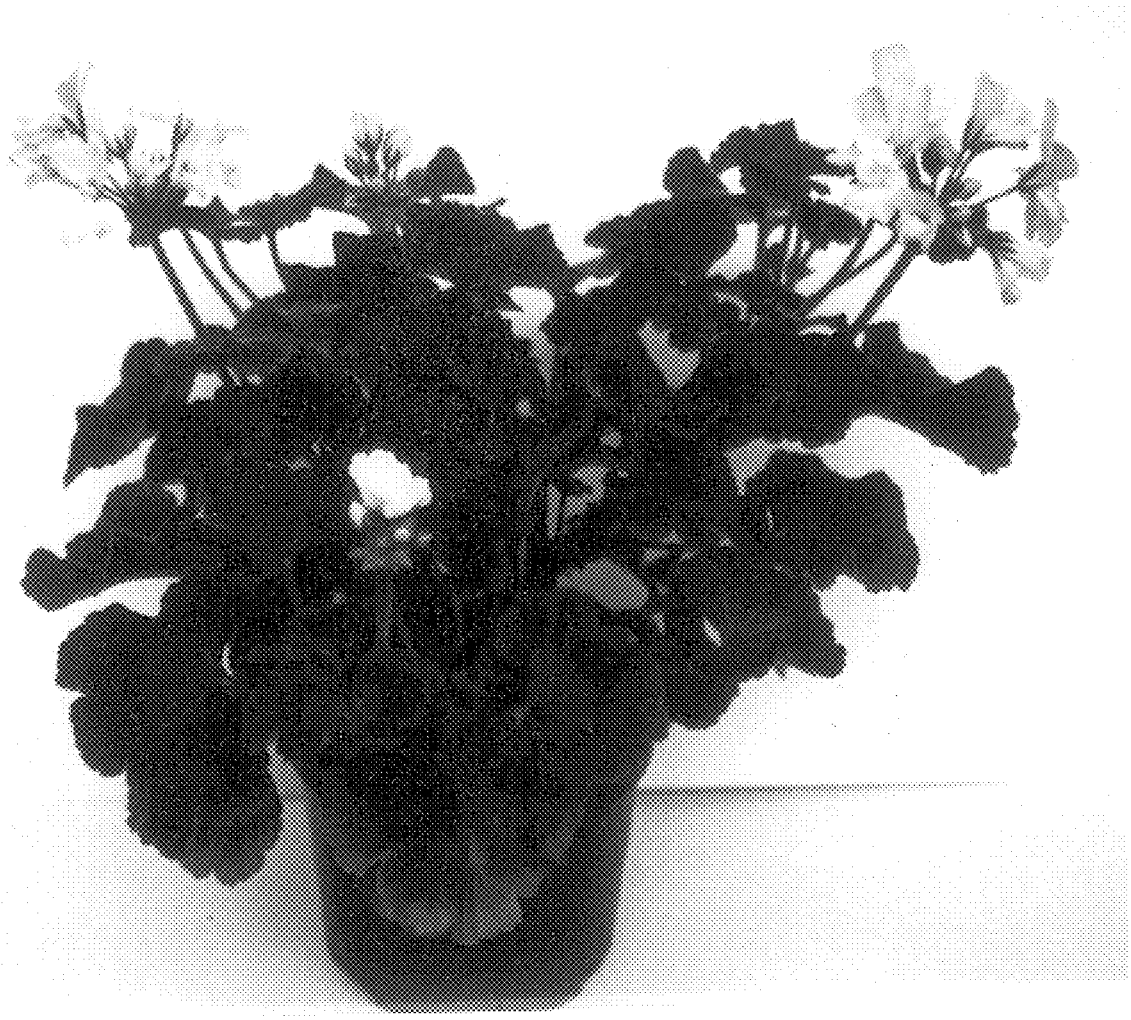

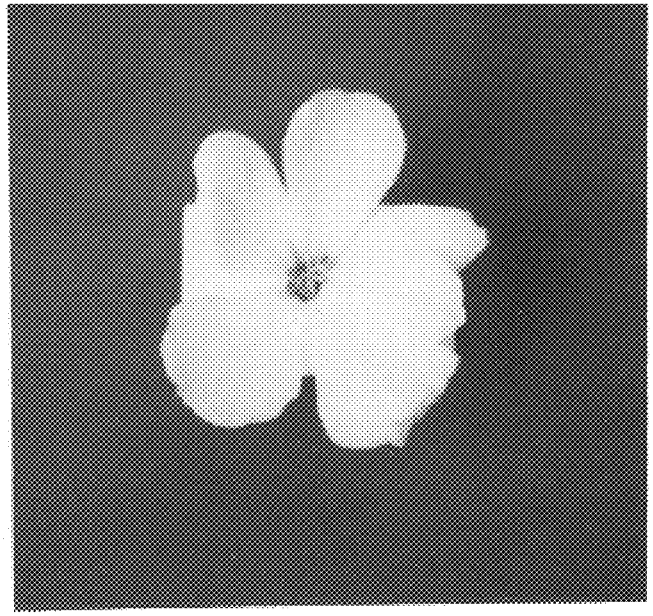
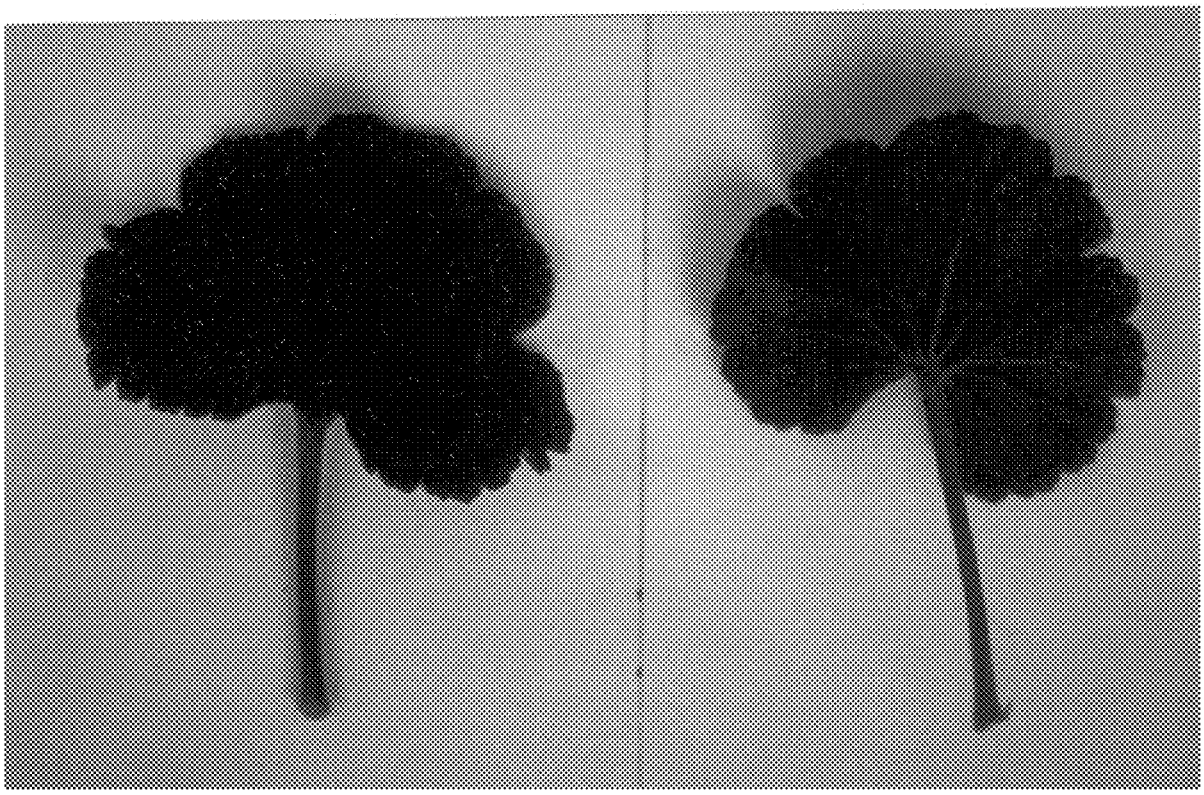

* * * * *